(12) United States Patent
Noy et al.

(10) Patent No.: US 7,940,393 B2
(45) Date of Patent: May 10, 2011

(54) METHOD AND SYSTEM FOR APPROXIMATING THE SPECTRUM OF A PLURALITY OF COLOR SAMPLES

(75) Inventors: Noam Noy, Natanya (IL); Yossi Shapira, Tel Aviv (IL)

(73) Assignee: Advanced Vision Technology (AVT) Ltd., Hod Hasharon (IL)

( * ) Notice: Subject to any disclaimer, the term of this patent is extended or adjusted under 35 U.S.C. 154(b) by 495 days.

(21) Appl. No.: 11/579,468

(22) PCT Filed: May 3, 2005

(86) PCT No.: PCT/IL2005/000466
§ 371 (c)(1),
(2), (4) Date: May 29, 2008

(87) PCT Pub. No.: WO2005/104659
PCT Pub. Date: Nov. 10, 2005

(65) Prior Publication Data
US 2008/0273202 A1   Nov. 6, 2008

Related U.S. Application Data

(60) Provisional application No. 60/568,298, filed on May 4, 2004.

(51) Int. Cl.
*G01N 21/25* (2006.01)
(52) U.S. Cl. .............. 356/408; 356/243.5; 356/402
(58) Field of Classification Search .......... 356/402, 356/243.1, 243.5, 408
See application file for complete search history.

(56) References Cited

U.S. PATENT DOCUMENTS

| | | | |
|---|---|---|---|
| 5,221,959 A * | 6/1993 | Ohyama et al. | 356/326 |
| 5,375,193 A * | 12/1994 | Adams, Jr. | 345/603 |
| 5,481,380 A | 1/1996 | Bestmann | |
| 5,596,428 A | 1/1997 | Tytgat et al. | |
| 5,596,510 A | 1/1997 | Boenke | |
| 5,696,839 A * | 12/1997 | Siegeritz | 382/162 |
| 5,801,854 A | 9/1998 | Naylor, Jr. | |
| 6,088,095 A * | 7/2000 | Sharma | 356/243.5 |
| 6,307,961 B1 | 10/2001 | Balonon-Rosen et al. | |
| 6,351,308 B1 * | 2/2002 | Mestha | 356/402 |
| 6,362,808 B1 | 3/2002 | Edge et al. | |
| 6,646,763 B1 | 11/2003 | Estrada | |
| 6,650,438 B1 | 11/2003 | Kress et al. | |
| 6,650,446 B1 | 11/2003 | Rozzi | |
| 6,654,150 B1 * | 11/2003 | Rozzi | 358/520 |
| 6,720,973 B2 | 4/2004 | Butler | |
| 2004/0090640 A1 | 5/2004 | Nino et al. | |

* cited by examiner

*Primary Examiner* — Tarifur Chowdhury
*Assistant Examiner* — Michael LaPage
(74) *Attorney, Agent, or Firm* — Merchant & Gould P.C.

(57) ABSTRACT

Method for approximating the spectrum of a plurality of color samples, the method including the procedures of measuring the color of a reference color sample in a color space, determining a reference sample estimated spectrum from the measured color, measuring the actual spectrum of the reference color sample, determining a spectral delta from the difference between the reference sample estimated spectrum and the actual spectrum, measuring the color of each of the color samples, for each of the color samples, determining a sample estimated spectrum from the measured color, and for each of the color samples, determining a sample approximated spectrum by adding the spectral delta to the respective sample estimated spectrum.

10 Claims, 2 Drawing Sheets

METHOD AND SYSTEM FOR APPROXIMATING THE SPECTRUM OF A PLURALITY OF COLOR SAMPLES

FIELD OF THE DISCLOSED TECHNIQUE

The disclosed technique relates to systems and methods for inspecting color samples, in general, and to systems and methods for converting color space values from one color space to another, in particular.

BACKGROUND OF THE DISCLOSED TECHNIQUE

Since the introduction of the CIE (Commission Internationale de l'Eclairage) color measurement system in the early 1930's, many different color spaces have been proposed for different applications. Color spaces differ in the parameters expressed on their coordinate axes and the manner in which the parameters are calculated. One CIE color space is the L*a*b* color space. In this color space, L* represents lightness, a* represents redness-greenness, and b* represents yellowness-blueness.

The approximate calculation of the conversion table occurs taking the pre-distortion of the measured color values and the spectral properties of the respective input apparatus into consideration. The transformed color values are compared to the calorimetrically defined color values of the test originals that are measured, for example, with a spectral photometer. Correction color values for the three-dimensional conversion table of the input color converter are calculated from the color value differences, the calculations being on the basis of an error compensating calculation.

L*a*b* readings produced from a red-green-blue (RGB) sensor by various methods are often not accurate due to the following reasons.

Lack of Information: The conversion between the RGB and the XYZ color spaces does not always create the correct L*a*b* value. The measured RGB is a result of two factors: (a) the Spectral graph of the measured object, and (b) the filter of the RGB measuring device (for example, camera). The filter of the RGB measuring device is two-dimensional. Therefore, there is a infinite number of spectral graphs that after filter multiplication will result in the same RGB values. Thus, different objects that may have two different spectral graphs may yield the same RGB values.

Diffusive illumination of RGB measuring device. In order to achieve consistent and accurate results, there are standard angles of both the sensor and the light source with respect to the inspected object. The reason for inaccuracy is that when using an RGB camera, the illumination is diffusive and not always meet the spectral conventional angles standards.

U.S. Pat. No. 6,720,973 B2 issued to Butler and entitled "Method and Apparatus for Transforming Color Gamut From One Color Space to Another", is directed to a system for transforming a digital color image from an RGB color space to a printer color space (i.e., CMYK color space). The system includes a color input device, a processor, a color output device, and a memory. The processor is connected with the color input device, the memory and with the color output device. The color input device provides the processor a plurality of data elements within the RGB color gamut, and the processor uses a look-up table stored in the memory, to find a correspondence to a data value in the printer color space. The processor provides the data value to the output device. The patent describes an algorithm for constructing the look-up table.

U.S. Pat. No. 6,646,763 B1 issued to Estrada, and entitled "Spectral Color Matching to a Device-Independent Color Value", is directed to a system for obtaining a spectral color match for a target color, using a set of colorants. The system includes a color matching engine which receives as input a target color value, a colorant look-up table, colorant characterization data, viewing conditions, and a threshold.

The target color value is a non-spectral representation of the target color to be produced by the color matching engine. The colorant look-up table includes an indexed list of sets of colorant concentrations. Each element in the list contains a set of color concentrations that specifies a mixture with a color, matching the index color. The colorant look-up table is indexed by coordinates in the color space in which the target color value is represented.

The colorant characterization data is a set of measurements of reflectance of visible light off of each of the colorants in the set of the colorants. The colorant characterization data defines the characteristics of each color in the set of the colorants. The viewing conditions specify the illumination under which a rendered color produced by the color matching engine is to be viewed. The viewing conditions can be either a set of default viewing conditions, or be specified by a user. The threshold specifies a maximum acceptable difference between the target color value and the rendered color which the color matching engine produces by mixing the set of the colorants, according to a set of colorant concentrations which the color matching engine determines.

The color matching engine produces the set of colorant concentrations, a quality of color match, and a rendered color reflectivity, according to the target color value, the colorant look-up table, the colorant characterization data, the viewing conditions, and the threshold, and according to an iterative process. The color matching engine produces the set of colorant concentrations for a mixture of colorants to match the target color value, according to the colorant look-up table. The quality of color match indicates the closeness of the match between the rendered color reflectivity and the target color represented by the target color value. The rendered color reflectivity is a calculated set of reflectance of visible light off of the rendered color.

U.S. Pat. No. 5,596,510 issued to Boenke and entitled "Table-Based Linear Interpolation for Color Correction System and Method", is directed to a method for converting a plurality of colors in the CMYK color space, to the corresponding colors in the RGB color space. According to this method, CMYK values are obtained for a color to be transformed, the CMYK values are scaled in the range of 0-255, a preselected number of most significant bits from each of the scaled CMYK values are extracted, and a delta look-up table is formed. The delta look-up table is produced according to nominal delta index values of the scaled CMYK values, wherein the nominal delta index values are the unselected least significant bits of the CMYK values.

According to a sampled look-up table, a nominal RGB value corresponding to the scaled CMYK value is determined. A delta value is determined to be combined with the nominal RGB value to produce a transform RGB representing the CMYK value, a restricted RGB value is determined according to a restriction look-up table, and a restricted RGB delta value is determined by subtracting the delta value from the nominal RGB value. The representation of the scaled CMYK value in the RGB color space is determined by subtracting the restricted RGB delta values from the nominal RGB values.

U.S. Pat. No. 6,650,438 B1 issued to Kress et al., and entitled "Construction of a Color Transform to Reduce Effects of Scanner Metamerism", is directed to a method for converting a raw RGB signal from a scanner, to a calibrated calorimetric space (e.g., CIE Lab color space). According to this method, a scanner scans a hard copy image and converts the hard copy image into a rectangular array of pixels, wherein each pixel contains red, green, and blue values. The raw RGB values can be converted to the CIE Lab color space, either by converting the RGB values to XYZ values by multiplying by a 3×3 matrix and converting the XYZ values to CIE Lab color values, or by converting the RGB values to the CIE Lab color values, directly by employing a 3D look-up table.

Reference Lab values of a target are measured by a spectrophotometer, and fed to a regression and interpolation procedure to obtain the 3×3 matrix or the 3D look-up table, thereby generating a calorimetric output. Before performing the regression and interpolatin procedure, different weighting factors are assigned to different areas of color gamuts for combinations of different colorants and media combinations. The weighting factors are determined according to the importance of the colorant or media, the importance of an area of the color space, and the position of the color gamut based on the gamut difference of the colorant or media.

U.S. Pat. No. 6,362,808 B1 issued to Edge et al., and entitled "Arrangement for Mapping Colors Between Imaging Systems and Method Therefor", is directed to a system for producing a color map to be used for transforming a color response of a source device, to another color response of a destination device. The system includes a computer arrangement connected to a memory and to the destination device. The computer arrangement includes a color management system. The color management system receives a source device profile and a destination device profile. The source device profile and the destination device profile describe mappings from device dependent color coordinate systems to device independent color coordinate systems.

The color management system processes the source device profile and the destination device profile to generate a color map, which describes the relationship between the source device and the destination device. The color management system employs the color map to transform a set of source coordinates in a device dependent source device color space, into a set of destination coordinates in a device dependent device color space.

The color management system includes a source device profile interpreter, a destination device profile interpreter and a color transformer. The color transformer is connected with the source device, the destination device, the source device profile interpreter and with the destination device profile interpreter. The source device profile interpreter receives a source device profile, and converts the source device profile in the source device color space, to a device independent color space known as a profile connecting space (PCS). The PCS is in the CIE Lab color space, and is used for converting the coordinates in the source device color space to the destination device color space.

The destination device profile interpreter receives a destination device profile to map color coordinates in a destination device color space used by the destination device, to XYZ tristimulus values. The destination device profile interpreter converts the color coordinates in the destination device color space to the PCS. The color transformer receives the PCS color coordinates from the source device profile interpreter and the destination device profile interpreter, to develop a color map that expresses a relationship between the color spaces used by the source device and the destination device.

U.S. Pat. No. 5,801,854 issued to Naylor, Jr., and entitled "Color Conversion Method" is directed to an algorithm for mapping colors from a cathode ray tube (CRT) color space to an inkjet color space, wherein the inkjet color space is more restricted than that of the CRT color space. A color which is at an edge of the CRT color space and outside the inkjet color space, is mapped to another edge of the inkjet color space, and a color which is within the CRT color space and outside the inkjet color space, is mapped to an edge of the inkjet color space. The mapping is optimized to make the relative distances between different colors in the image to remain the same.

U.S. Pat. No. 5,596,428 issued to Tytgat et al., and entitled "Color Matching by Systems Calibration, Linear and Non-Linear Gamut Mapping", is directed to a method to reproduce an image on a color monitor to another image in a thermo-sublimation color printer, while preserving the colors which are presented on the monitor. The monitor displays an X-ray or a computer tomography (CT) image of an organ of a patient, such as a bone, in gray scale, while the vasculature is presented in color.

A first coordinate value c of the thermosublimation color printer is proportional to the amount of heat applied to a thermal head of the thermosublimation color printer, to transfer dye from a cyan dye donor to a hard copy. A second coordinate value m of the thermosublimation color printer is proportional to the amount of heat applied to the thermal head, to transfer dye from a magenta dye donor to the hard copy. A third coordinate value y of the thermosublimation color printer is proportional to the amount of heat applied to the thermal head, to transfer dye from a yellow dye donor to the hard copy. In this manner, an output color signal $o=(c,m,y)$ is defined. An input color signal i can be represented as a device coordinate $i=(R,G,B)$. The color c observed on the color monitor is measured and represented in a device independent tristimulus color coordinate system, such as the CIE XYZ, or by three polar coordinates of lightness, hue, and saturation $(L,H,S)$.

According to this method, a first transformation model $c=M(i)$ is formed to transform an input color signal $i=(R,G,B)$, to a color signal $c=(L,H,S)$. A second transformation model $c'=P(o)$ is formed to transform the output color signal $o=(c,m,y)$ to color coordinates $c'=(L',H',S')$. A first transformation unit transforms input color signal i to the color signal c, according to transformation model $M(i)$. The color signal c represents the color in which the input signal i is represented in the color monitor. This color signal c must be obtained on the thermosublimation color printer. A gamut transformation unit transforms c to c'. Since the transformation model $c'=P(o)$ is known, the output color signal o can be obtained from the color signal c', by inversion of the transformation P: $o=P^{-1}(c')$. In this manner, a corresponding output color signal $o=(c,m,y)$ is determined, to obtain the color coordinates $c'=(L',H',S')$.

U.S. Pat. No. 5,481,380 issued to Bestmann, and entitled "Method and Apparatus for Calibration of Color Values", is directed to a system for converting RGB color values in an apparatus dependent color space of an input apparatus, to Lab color values of the CIE LAB in an apparatus independent color space of an output apparatus. The system includes a scanner, a camera, a video, a 3D input color converter, an image processing unit, an operating terminal, a communication unit, an output color converter, a monitor, a color separation recorder, and a proof recorder.

The 3D input color converter is connected with the scanner, the camera, the video, and with the image processing unit. The output color converter is connected with the image processing unit, the monitor, the color separation recorder, and with the proof recorder. The image processing unit is connected with the operating terminal, and with the communication unit.

The 3D input color converter converts the RGB color values of the input apparatus (i.e., the scanner, the camera, and the video), to the Lab color values of the output apparatus (i.e., the monitor, the color separation recorder, and the proof recorder). The 3D input color converter includes a look-up table for converting the RGB color values to the Lab color values. The image processing unit performs color corrections and geometric processing on the basis of colors which the 3D input color converter transforms, according to an input from a user, via the operating terminal. The image processing unit stores the color values which are to be processed, in the communication unit.

SUMMARY OF THE PRESENT DISCLOSED TECHNIQUE

It is an object of the disclosed technique to provide a novel method and system for measuring the spectral properties of printed material, inline. According to an aspect of the disclosed technique, there is thus provided a method for approximating the spectrum of a plurality of color samples. The method includes the procedures of measuring the color of a reference color sample in a color space, determining a reference sample estimated spectrum from the measured color, and measuring the actual spectrum of the reference color sample.

The method further includes the procedures of determining a spectral delta from the difference between the reference sample estimated spectrum and the actual spectrum, and measuring the color of each of the color samples. The method further includes the procedures of determining a sample estimated spectrum from the measured color, for each of the color samples, and determining a sample approximated spectrum for each of the color samples, by adding the spectral delta to the respective the sample estimated spectrum.

According to another aspect of the disclosed technique, there is thus provided a system for approximating the spectrum of a plurality of color samples. The system includes a spectrophotometer, an image acquisition device, and a controller coupled with the image acquisition device and with the spectrophotometer. The spectrophotometer measures the actual spectrum of at least one reference color sample selected from the color samples, in a spectral color space. The image acquisition device measures the color of the color samples in a color space.

The controller determines a sample estimated spectrum from the measured color for each of the color samples, and a spectral delta from the difference between the sample estimated spectrum and the actual spectrum of each reference color sample. Furthermore, for each non-selected ones of the color samples, the controller determines a sample approximated spectrum by adding the spectral delta to the sample estimated spectrum.

BRIEF DESCRIPTION OF THE DRAWINGS

The disclosed technique will be understood and appreciated more fully from the following detailed description taken in conjunction with the drawings in which.

DETAILED DESCRIPTION OF THE EMBODIMENTS

The disclosed technique overcomes the disadvantages of the prior art by providing a novel system and method for approximating the spectrum of a plurality of color samples. According to the disclosed technique, an approximated spectrum is determined, by measuring the actual spectrum of a reference color sample, measuring color of a selected color sample in a given color space (e.g., red-green-blue—RGB, cyan-yellow-magenta-black—CYMK), determining an estimated spectrum from the measured color and determining a spectral delta from the difference between the estimated spectrum and the actual spectrum. Then, the color of a plurality of color samples is measured, their respective spectrum estimated and then further approximated by adding the previously determined spectral delta to the estimated spectrum.

Figure 1:
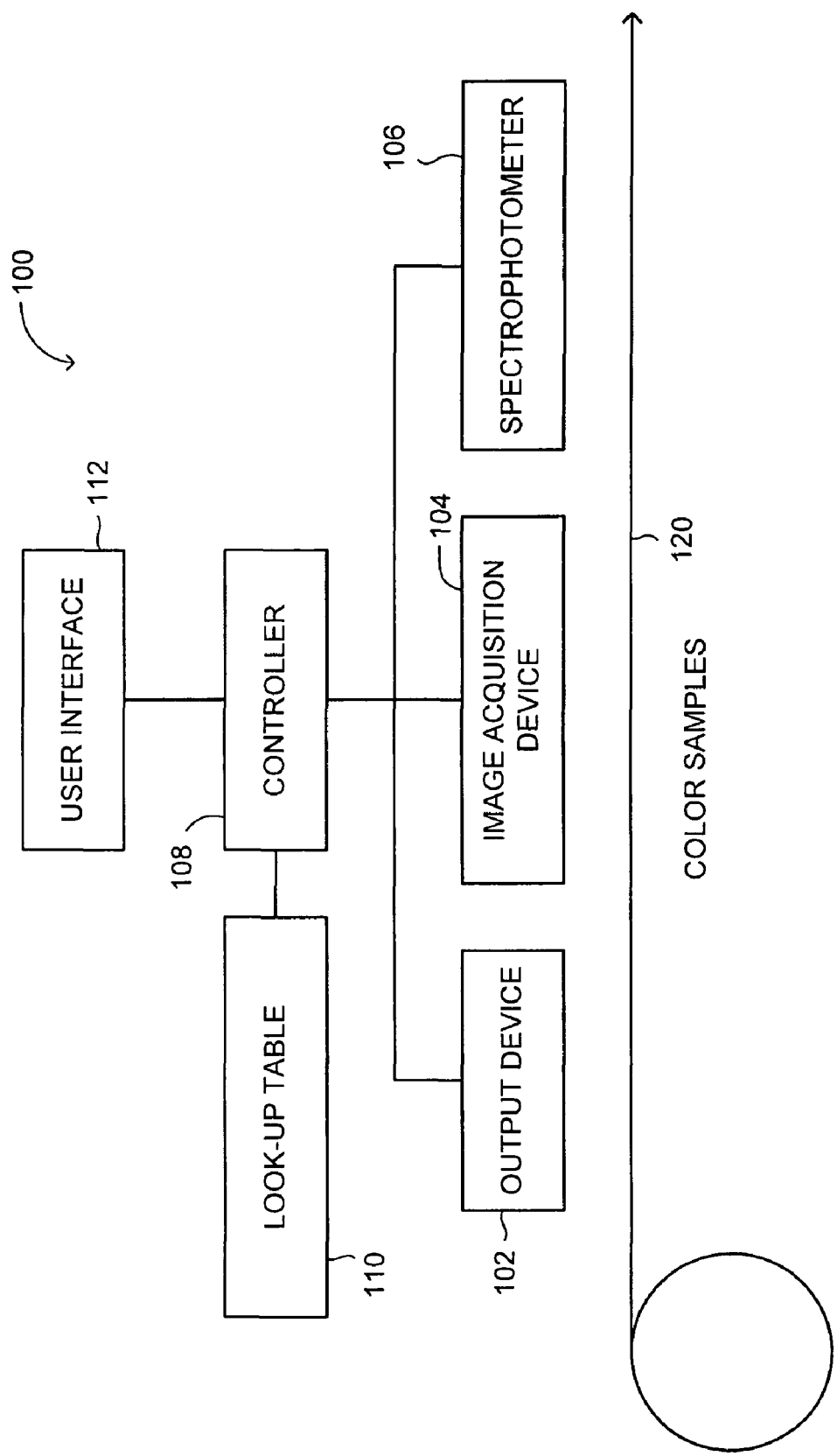
FIG. 1 is a schematic illustration of a system, for approximating spectrum measurements, constructed and operative in accordance with an embodiment of the disclosed technique.

Reference is now made to FIG. 1, which is a schematic illustration of a system, generally referenced 100, for approximating spectrum measurements, constructed and operative in accordance with an embodiment of the disclosed technique. System 100 includes an output device 102, an image acquisition device 104 (e.g., a camera, a scanner, an array of filtered color detectors, calorimeter, spectrophotometer), a spectrophotometer 106, a controller 108, a Look-Up Table 110 and a user interface 112. The camera can be a charge-coupled device (CCD), complementary metal-oxide semiconductor (CMOS), and the like. It is noted that image acquisition device 104 is characterized by being operative to produce a color reading much faster than spectrophotometer 106 produces a spectral reading, of the same sample. User interface 112 may be, for example, a computer having a screen, a mouse, a keyboard, speakers and a microphone. The output device can be for example a printer, a material mixer, a material processing system, or any device which is operative to set the color of samples 120, according to an output of controller 108.

Controller 108 is coupled with output device 102, image acquisition device 104, spectrophotometer 106, Look-Up Table 110 and user interface 112.

The spectrophotometer 106 measures the actual spectrum of at least one reference color sample (i.e., reference samples) selected from a plurality of color samples 120. This spectral measurement is represented in L.a.b. color space. Image acquisition device 104 measures the color of the color samples, in a non-L.a.b. color space (e.g., RGB, CYMK, proprietary color space).

Controller 108 determines an estimated spectrum (i.e., estimated L.a.b.) from the measured color for each of the reference samples either by a conversion function or by using Look-Up Table 110. It is noted that this conversion is regarded inaccurate and needs further approximation. Controller 108 further determines a spectral delta, from the difference between the estimated spectrum (i.e., estimated L.a.b.) and the actual spectrum (i.e., measured L.a.b.) of the reference samples. This spectral delta is later used to correct and approximate calculated L.a.b. color values. For each of the rest of the color samples, the controller 108 approximates the spectrum by adding the spectral delta, to the estimated spectrum derived from respective color measurements of these samples, acquired by image acquisition device 104.

Figure 2:
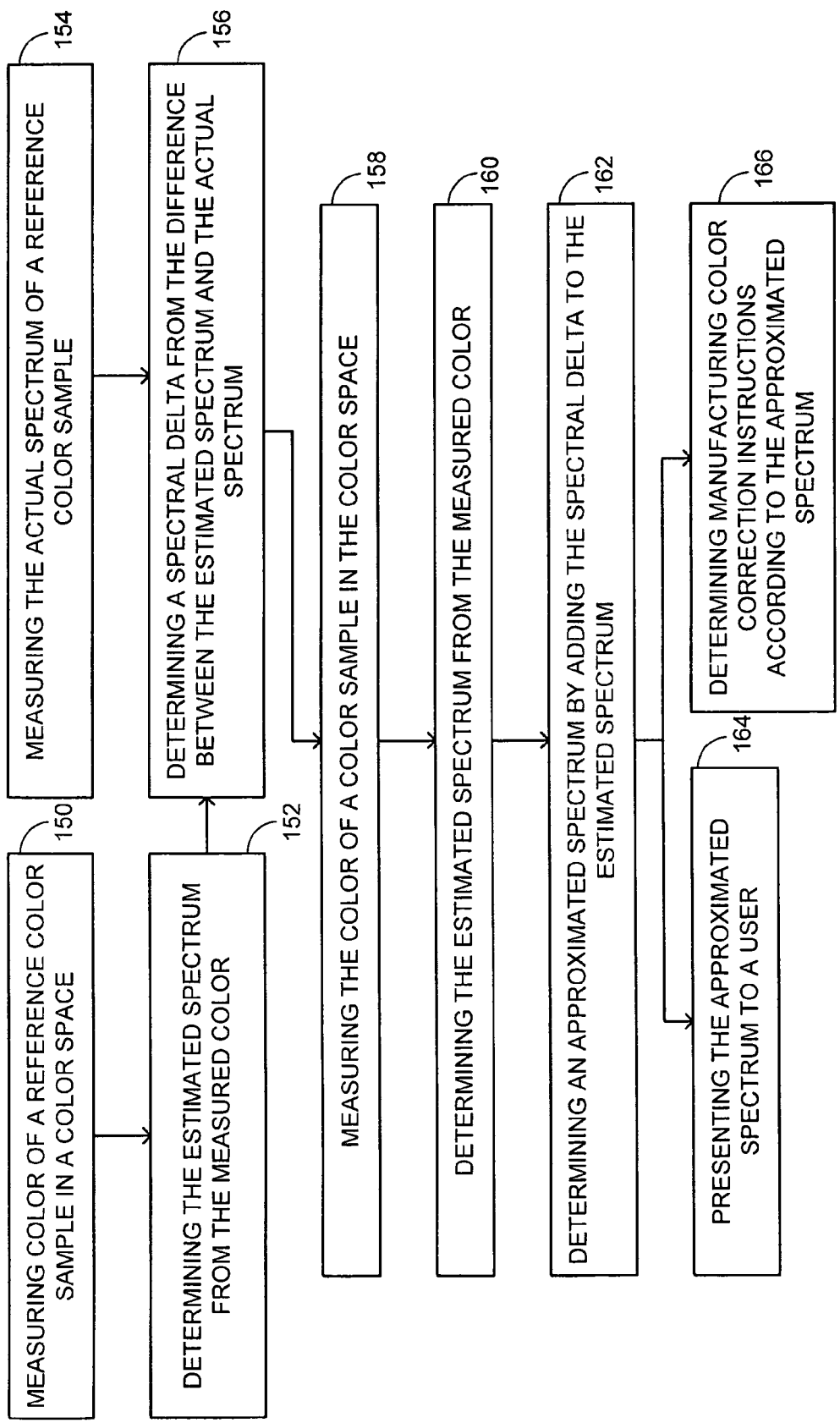
FIG. 2 is a schematic illustration of a method for approximating the spectrum of a plurality of color samples, operative in accordance with another embodiment of the disclosed technique.

Reference is now made to FIG. 2, which is a schematic illustration of a method for approximating the spectrum of a plurality of color samples, operative in accordance with another embodiment of the disclosed technique. In procedure 150, the color of a selected reference color sample is being measured in a color space. It is noted that more than one color sample can be used as reference. A color sample may be a printed object, a three dimensional object, a projection of light (i.e., when testing display devices), and the like. In the example set forth by system 100 of FIG. 1, image acquisition device 104 measures the color of a selected reference color sample in an RGB color space.

In procedure 152, the estimated spectrum of the measured color is determined. With reference to FIG. 1, controller 108 converts the color measurement values, acquired in procedure 152, into estimated spectral values (i.e., L.a.b.). Controller 108 can determine the estimated spectrum from the measured color 152 by using Look-Up Table 110, or by an analytical conversion.

In procedure 154, the actual spectrum of the same selected color sample is measured. With reference to FIG. 1, spectrophotometer 106 measures the actual spectrum of that selected reference color sample.

In procedure 156, a spectral delta from the difference between the estimated spectrum and the actual spectrum is determined. This spectral delta can be presented in a variety of formats (e.g., vectorial). With reference to FIG. 1, controller 108 determines the spectral delta from the difference between the estimated spectrum and the actual spectrum.

In procedure 158, the color of a color sample in the color space, is measured. With reference to FIG. 1, image acquisition device 104 measures the color of a color sample in the color space In procedure 160, the estimated spectrum from the measured color (i.e., measured in procedure 158) is determined. With reference to FIG. 1, controller 108 converts the color measurement values, acquired in procedure 158, into estimated spectral values (i.e., L.a.b.). Controller 108 can determine the estimated spectrum from the measured color 152 by using Look-Up Table 110, or by an analytical conversion.

In procedure 162, an approximated spectrum is determined, by adding the spectral delta to the estimated spectrum. With reference to FIG. 1, controller 108 determines the approximated spectrum of the color sample, whose color was acquired and measured in procedure 158, by adding the spectral delta to the estimated spectrum.

In procedure 164, the approximated spectrum is presented to a user. With reference to FIG. 1, controller 108 provides information relating to the approximated spectrum, to user interface 112, which in turn provides this information to the user (e.g., visually, audibly).

In procedure 164, manufacturing color correction instructions are determined according to the approximated spectrum. With reference to FIG. 1, controller 108 determines manufacturing color correction instructions according to the approximated spectrum. These manufacturing color correction instructions can be provided to a manufacturing system, such as a printer, a material mixer (e.g., in the plastic industry), a material processing system (e.g., anodizing facility) or any device which is operative to control the color of the sample.

It will be appreciated by persons skilled in the art that the disclosed technique is not limited to what has been particularly shown and described hereinabove. Rather the scope of the disclosed technique is defined only by the claims, which follow.

The invention claimed is:

1. A method for approximating the spectrum of a plurality of color samples, the method comprising the procedures of:
    measuring the color of a reference color sample in a color space;
    determining a reference sample estimated spectrum from said measured color of the reference color sample;
    measuring the actual spectrum of said reference color sample;
    determining a spectral delta from the difference between said reference sample estimated spectrum and said actual spectrum;
    measuring the color of each of said color samples;
    for each of said color samples, determining a sample estimated spectrum from said measured color of each of said color samples; and
    for each of said color samples, determining a sample approximated spectrum by adding said spectral delta to the respective said sample estimated spectrum.

2. The method according to claim 1, further comprising the procedure of presenting said sample approximated spectrum to a user.

3. The method according to claim 1, further comprising the procedure of determining manufacturing color correction instructions according to said sample approximated spectrum.

4. The method according to claim 1, wherein said color space is RGB.

5. The method according to claim 1, wherein said actual spectrum is presented as L*a*b*.

6. The method according to claim 1, wherein said procedure of measuring the color of said reference color sample, and said procedure of measuring the color of each of said color samples, are performed by the same image acquisition device.

7. A system for approximating the spectrum of a plurality of color samples, the system comprising:
    a spectrophotometer, measuring an actual spectrum of at least one reference color sample selected from said color samples, in a spectral color space;
    an image acquisition device, measuring the color of said at least one reference color sample, in a color space; and
    a controller coupled with said image acquisition device and with said spectrophotometer, said controller determining a reference sample estimated spectrum from said measured color for each of said reference color samples, said controller determining a spectral delta from the difference between said reference sample estimated spectrum and said actual spectrum of each of said at least one reference color sample, for each non-selected ones of said color samples, determining a sample estimated spectrum from said color samples, said controller determining a sample approximated spectrum by adding said spectral delta to said sample estimated spectrum.

8. The system according to claim 7, further comprising a user interface coupled with said controller.

9. The system according to claim 7, further comprising an output device coupled with said controller, said output device setting the color of said color samples, according to an output respective of said controller.

10. The system according to claim 7, wherein said image acquisition device is selected from the list consisting of:
    camera;
    scanner;
    array of filtered color detectors;
    colorimeter; and
    spectrophotometer.

* * * * *